United States Patent [19]

Hidaka et al.

[11] Patent Number: 5,128,133
[45] Date of Patent: Jul. 7, 1992

[54] INDUSTRIAL MICROBICIDAL/MICROBISTATIC COMPOSITION AND USE THEREOF

[75] Inventors: Yasuhiro Hidaka; Masanobu Takahashi, both of Osaka; Toshio Sato, Oita, all of Japan

[73] Assignee: Yoshitomi Pharmaceutical Industries, Ltd., Osaka, Japan

[21] Appl. No.: 616,954

[22] Filed: Nov. 21, 1990

[30] Foreign Application Priority Data

Nov. 21, 1989 [JP] Japan .................. 1-304215

[51] Int. Cl.⁵ .................... A01N 25/00; C02F 1/00
[52] U.S. Cl. ........................ 424/405; 424/406; 514/441; 514/634
[58] Field of Search ............ 514/441, 634, 372, 311; 424/405, 406; 162/161; 210/764; 530/205

[56] References Cited

U.S. PATENT DOCUMENTS

| | | | |
|---|---|---|---|
| 4,289,581 | 9/1981 | Katayama et al. | 514/441 |
| 4,466,975 | 8/1984 | Magami et al. | 424/270 |
| 4,518,610 | 5/1985 | Umekawa et al. | 514/516 |
| 4,647,577 | 3/1987 | Umekawa et al. | 514/441 |
| 4,725,623 | 2/1988 | Whitekettle et al. | 514/634 |
| 4,879,306 | 11/1989 | Henkels et al. | 514/441 |

FOREIGN PATENT DOCUMENTS 1091049  11/1967  United Kingdom .

OTHER PUBLICATIONS

Derwent Abstract of WPI No. 77-33799Y/19 of Japanese Patent Examined Publication (Kokoku) No. 14294/1977, first published Oct. 1, 1975 as Japanese Patent Unexamined Pub. (Kokai) No. 125025/1975.
Derwent Abstract of WPI No. 81-06713D/05 of Japanese Patent Examined Publication (Kokoku) No. 16084/1982, first published Nov. 26, 1980 as Japanese Patent Unexam. Pub. (Kokai) No. 151502/1980 No.
Derwent Abstract of WPI No. 81-63194D/35 of Japanese Patent Examined Publication (Kokoku) 42603/1982, first published Jul. 13, 1981 as Japanese Pat. Unexam. Publ. (Kokai) No. 86106/1981.
Derwent Abstract of WPI No. 85-041548/07 of Japanese Patent Unexamined Publication (Kokai) No. 1105/1985, published on Jan. 7, 1985.

Primary Examiner—Thurman K. Page
Assistant Examiner—D. Colucci
Attorney, Agent, or Firm—Sughrue, Mion, Zinn Macpeak & Seas

[57] ABSTRACT

An industrial microbicidal/microbistatic composition which comprises (1) 4,5-dichloro-1,2-dithiol-3-one and (2) N-dodecylguanidine hydrochloride or N-dodecylguanidine acetate and a method of killing or inhibiting the growth of microbe or controlling slime formation using said composition.

6 Claims, No Drawings

INDUSTRIAL MICROBICIDAL/MICROBISTATIC COMPOSITION AND USE THEREOF

BACKGROUND OF THE INVENTION

It is known that an organic matter such as heavy oil sludges, cutting oils or textile oils, exists in water, microorganisms such as gram positive bacteria, gram negative bacteria, yeast or fungi in water degrade or denature the organic matter, producing various problems. For example, slime generates on a heat exchanger surface in circulating water cooling systems and in the cooling drainpipe in petrochemical and chemical and chemical plants, blocking up said pipe and thereby causing significant decreases in cooling capacity. Moreover, microorganisms such as gram positive bacteria, gram negative bacteria, yeast or fungi generated in white water in papermaking plants grow and product slime. When the slimes exfoliate and get mixed in paper products, they cause such various troubles as that the paper is used to break, stains spotwise and smells in the paper-rolling process.

Japanese Patent Examined Publication (Kokoku) No. 14294/1977 discloses that 4,5-dichloro-1,2-dithiol-3-one of the formula:

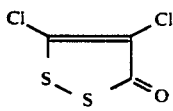

(hereinafter sometimes referred to as "dithiol compound") is effective in preventing slime formation caused by microorganisms such as gram positive bacteria, gram negative bacteria, yeast or fungi in industrial water systems, particularly, in process water systems in paper mills and in cooling water systems, and the dithiol compound has already been put into practical use.

The dithiol compound itself exerts simultaneously and instantaneously the microbicidal effects when added to the water system. However, the dithiol compound is apt to decompose thereafter, and does not always exhibit long-lasting microbicidal activity. Therefore, it is unpractical to use the dithiol compound alone. Further, since the dithiol compound is a relatively expensive agent, it is desirable to use in an amount as small as possible.

The microbicidal/microbistatic agents for industrial use are generally toxic to human beings and animals, and cause environmental pollution by contaminating waste matter. Therefore, it has recently been required that such agents be used at a concentration as low as possible.

Accordingly, it has been attempted to decrease the amount of the dithiol compound and exhibit a synergistic effect by a combination of 4,5-dichloro-1,2-dithiol-3-one with bis(tribromomethyl) sulfone (Japanese Patent Examined Publication (Kokoku) No. 16084/1982), 2-bromo-2-nitropropane-1,3-diol (Japanese Patent Examined Publication (Kokoku) No. 42603/1982), haloacetic acid esters (U.S. Pat. No. 4,647,577), alkylene bisthiocyanates (U.S. Pat. No. 4,518,610), 1,2-benzisothiazolin-3-one (U.S. Pat. No. 4,466,975), isothiazolone salts (Japanese Patent Unexamined Publication (Kokai) No. 1105/1985) or dibromonitrilopropionamide (U.S. Pat. No. 4,879,306).

On the other hand, British Patent Publication No. 1091049/1968 discloses that N-dodecylguanidine hydrochloride is usable in a microbistatic paper and Japanese Patent Unexamined Publication (Kokai) No. 76867/1977 discloses a method of preventing industrial materials and other materials and articles from microbe-caused troubles by using films and sheets containing N-dodecylguanidine hydrochloride.

As mentioned above, various attempts have been made to develop microbicidal/microbistatic compositions capable of exhibiting patent and long-lasting microbicidal/microbistatic effects and achieve a decrease of the amount of the dithiol compound. However, it is still desired to develop an improved microbicidal/microbistatic composition for industrial use containing the dithiol compound.

SUMMARY OF THE INVENTION

The compositions and method according to the present invention are practically useful for controlling slime in process water of papermaking and industrial cooling water and also for the microbicidal/microbistatic treatment of various industrial materials, such as heavy oils sludges, cutting oils, textile oils and the like.

DETAILED DESCRIPTION OF THE INVENTION

The present invention relates to an industrial microbicidal/microbistatic composition which comprises (1) 4,5-dichloro-1,2-dithiol-3-one and (2) N-dodecyguanidine hydrochloride, or N-dodecyguanidine acetate and a method of killing or inhibiting the growth of microbes which comprises adding (1) 4,5-dichloro-1,2-dithiol-3-one and (2) N-dodecyguanidine hydrochloride or N-dodecyguanidine acetate to a system to be controlled microbicidally/microbistatically.

The two ingredients, namely, (1) 4,5-dichloro-1,2-dithiol-3-one and (2) N-dodecyguanidine hydrochloride or N-dodecyguanidine acetate, may be added simultaneously or separately to the media or materials to be treated microbicidally.

Said compositions can be prepared by dissolving the active ingredients in an appropriate solvent such as N-methyl-2-pyrrolidone, dimethylformamide, mono- or poly-alkylene glycol (e.g., ethylene glycol, propylene glycol, diethylene glycol or dipropylene glycol), mono- or poly-alkylene glycol methyl ether (e.g., ethylene glycol monomethyl ether, ethylene glycol monoethyl ether, ethylene glycol monophenyl ether, propylene glycol monomethyl ether, diethylene glycol monomethyl ether, dipropylene glycol monomethyl ether and tripropylene glycol monomethyl ether) or a mixture thereof. N-methyl-2-pyrrolidone is one of preferred solvents from the viewpoints of the solubility of N-dodecylguanidine hydrochloride or N-dodecylguanidine acetate therein and the physical properties thereof.

It is recommendable that a surfactant be further added to such composition comprising 4,5-dichloro-1,2-dithiol-3-one and N-dodecylguanidine hydrochloride or N-dodecylguanidine acetate in the organic solvent or the mixed organic solvent. Said surfactant may be an ordinary dispersing agent and preferably is a nonionic or anionic surfactant selected from among higher alcohol-ethylene oxide adducts, alkylphenolethylene oxide, coco fatty acid diethanolamides, ethylenediamine-ethylene oxide, propylene oxide block copolymers, aromatic sulfonic acid salts such as sodium decylbenzenesulfonate, sodium N-dodecylbenzenesulfonate and sodium dibutylnaphtalenesulfonate, alkyl sulfuric acid salts such as sodium octyl sulfate, sodium N-dodecyl sulfate, sodium decyl sulfate and sodium tetradecyl sulfate and the like.

In applying the method of the present invention, 4,5-dichloro-1,2-dithiol-3-one and N-dodecylguanidine hydrochloride or N-dodecylguanidine acetate are either used in the form of a composition such as mentioned above containing both the active ingredients preferably in a weight ratio of 95:5–5:95, more preferably about 1:9–4:1 at an addition level of about 0.5–20 ppm or are added separately to attain such mixing ratio and addition level, whereby slime formation can be prevented. As a result of such combined use, the amount of each ingredients can be significantly decreased.

The composition and the method of the present invention can be used not only in process water systems in papermaking, in industrial cooling water systems, but also in washing water, heavy oil sludges, cutting oils, lignin-containing waste liquors, aqueous paints, antifouling paints, latexes, textile oils and other liquid targets and further can be used for, e.g., starch, fibrous wall materials, and other solids in order to kill, prevent or inhibit the growth of microorganisms such as gram positive bacteria, gram negative bacteria, yeast or fungi.

Moreover, the composition of the present invention can be used with other microbicidal agents and so forth.

The following experimental examples demonstrate the enhanced microbicidal activities of the microbicidal/microbistatic composition for industrial use of the present invention.

EXPERIMENTAL EXAMPLE 1

A bouillon medium was inoculated with *Bacillus subtilis* (Gram positive bacteria) as a test microorganism and incubated at 37° C. for 16 hours and then thereto were added a mixture of 4,5-dichloro-1,2-dithiol-3-one and N-dodecylguanidine hydrochloride in each concentration shown in Table 1.

After adding, the value of adenosine 3'-phosphate (hereinafter referred to as ATP) was measured by using an ATP measuring kit (NU-200) using a lumicounter 1000 (Nichion Irika-kiki Selsakusho).

In this experimental example, the value of ATP shows a relative value of ATP in each test sample and means an index of the number of viable microbial cells in each test sample. The smaller the number of viable cells is, the stronger the microbial effect of the test compound is.

The results are shown in Table 1. Throughout the experiments, the value of ATP for sterile water was 183 and the value of ATP for a mixture of sterile water and a bouillon medium was 312.

TABLE 1

| | Test Compound | ATP value after adding | | |
|---|---|---|---|---|
| | | 5 min. | 15 min. | 30 min. |
| Composition of the present invention | 4,5-dichloro-1,2-dithiol-3-one 0.3 ppm + N-dodecylguanidine HCl 0.3 ppm | 3,140 | 2,850 | 2,440 |
| Composition of the present invention | 4,5-dichloro-1,2-dithiol-3-one 0.5 ppm + N-dodecylguanidine HCl 0.5 ppm | 3,020 | 2,620 | 2,180 |
| Composition for | 4,5-dichloro-1,2-dithiol-3-one | | | |

TABLE 1-continued

| | Test Compound | ATP value after adding | | |
|---|---|---|---|---|
| | | 5 min. | 15 min. | 30 min. |
| comparison | 0.3 ppm | 9,016 | 10,100 | 12,740 |
| | 1 ppm | 8,100 | 3,386 | 2,970 |
| | 2 ppm | 3,170 | 2,680 | 2,840 |
| Composition for comparison | N-dodecylguanidine HCl | | | |
| | 0.3 ppm | 12,000 | 11,400 | 11,530 |
| | 1 ppm | 3,550 | 3,010 | 2,970 |
| | 2 ppm | 3,460 | 2,750 | 2,840 |
| | none | 19,700 | 21,050 | 22,600 |

EXPERIMENTAL EXAMPLE 2

By using *Pseudomonas aeruginosa* as a gram negative test microorganism, the test was similarly carried out as Experimental Example 1.

The results are shown in Table 2.

TABLE 2

| | Test Compound | ATP value after adding | | |
|---|---|---|---|---|
| | | 5 min. | 15 min. | 30 min. |
| Composition of the present invention | 4,5-dichloro-1,2-dithiol-3-one 0.3 ppm + N-dodecylguanidine HCl 0.3 ppm | 1,280 | 1,120 | 920 |
| Composition of the present invention | 4,5-dichloro-1,2-dithiol-3-one 0.3 ppm + N-dodecylguanidine HCl 0.3 ppm | 910 | 780 | 630 |
| Composition for comparison | 4,5-dichloro-1,2-dithiol-3-one | | | |
| | 0.3 ppm | 9,060 | 7,100 | 6,140 |
| | 1 ppm | 4,490 | 2,650 | 1,160 |
| | 2 ppm | 2,520 | 1,930 | 1,140 |
| Composition for comparison | N-dodecylguanidine HCl | | | |
| | 0.3 ppm | 7,110 | 6,220 | 6,140 |
| | 1 ppm | 2,530 | 2,310 | 1,950 |
| | 2 ppm | 1,840 | 1,550 | 1,000 |
| | none | 19,700 | 21,050 | 22,600 |

The Experimental Examples and other experiments have revealed that the industrial microbicidal/microbistatic composition containing 4,5-dichloro-1,2-dithiol-3-one and N-dodecylguanidine hydrochloride or N-dodecylguanidine acetate as active ingredients shows stronger synergistic effect as compared with the use of each active ingredient alone and that the combined active ingredients can bring about a strong microbicidal effect in very small amounts.

The present invention will be more concretely explained by the following examples, but they should not be thought to limit the scope of the invention.

| | percent by weight |
|---|---|
| Example 1 | |
| 4,5-dichloro-1,2-dithiol-3-one | 1 |
| N-dodecylguanidine hydrochloride | 9 |
| diethyleneglycol | 89.5 |
| coco fatty acid diethanolamide (coco fatty acid:diethanolamine = 1:1) | 0.5 |
| Example 2 | |
| 4,5-dichloro-1,2-dithiol-3-one | 6 |
| N-dodecylguanidine hydrochloride | 1.5 |
| diethyleneglycol | 92 |
| coco fatty acid diethanolamide (coco fatty acid:diethanolamine = 1:1) | 0.5 |
| Example 3 | |

-continued

|  | percent by weight |
|---|---|
| 4,5-dichloro-1,2-dithiol-3-one | 1 |
| N-dodecylguanidine hydrochloride | 9 |
| N-methyl-2-pyrrolidone | 1 |
| diethyleneglycol monomethyl ether | 88.5 |
| coco fatty acid diethanolamide | 0.5 |
| (coco fatty acid:diethanolamine = 1:1) | |
| Example 4 | |
| 4,5-dichloro-1,2-dithiol-3-one | 6 |
| N-dodecylguanidine hydrochloride | 1.5 |
| diethyleneglycol monomethyl ether | 92 |
| coco fatty acid diethanolamide | 0.5 |
| (coco fatty acid:diethanolamine = 1:1) | |
| Example 5 | |
| 4,5-dichloro-1,2-dithiol-3-one | 1 |
| N-dodecylguanidine acetate | 9 |
| diethyleneglycol | 89.5 |
| coco fatty acid diethanolamide | 0.5 |
| (coco fatty acid:diethanolamine = 1:1) | |
| Example 6 | |
| 4,5-dichloro-1,2-dithiol-3-one | 6 |
| N-dodecylguanidine acetate | 1.5 |
| diethyleneglycol | 92 |
| coco fatty acid diethanolamide | 0.5 |
| (coco fatty acid:diethanolamine = 1:1) | |
| Example 7 | |
| 4,5-dichloro-1,2-dithiol-3-one | 1 |
| N-dodecylguanidine acetate | 9 |
| N-methyl-2-pyrrolidone | 1 |
| diethyleneglycol monomethyl ether | 88.5 |
| coco fatty acid diethanolamide | 0.5 |
| (coco fatty acid:diethanolamine = 1:1) | |
| Example 8 | |
| 4,5-dichloro-1,2-dithiol-3-one | 6 |
| N-dodecylguanidine acetate | 1.5 |
| diethyleneglycol monomethyl ether | 92 |
| coco fatty acid diethanolamide | 0.5 |
| (coco fatty acid:diethanolamine = 1:1) | |

What is claimed is:

1. An industrial microbicidal/microbistatic composition for controlling slime in process water of papermaking and industrial cooling water and treatment of industrial materials consisting of washing water, heavy oil sludges, cutting oils, lignin-containing waste liquors, aqueous paints, antifouling paints, latexes and textile oils, which comprises:
   1–70 parts by weight of (1) 4,5-dichloro-1,2-dithiol-3-one and (2) N-dodecylguanidine hydrochloroide or N-dodecylguanidine acetate as active ingredients, wherein the weight ratio of 4,5-dichloro-1,2-dithiol-3-one and N-dodecylguanidine hydrochloride or N-dodecylguanidine acetate is 95:5–5:95,
   a surfactant, and
   a sufficient amount of a solvent to make 100 parts by weight of the composition.

2. The composition as claimed in claim 1, wherein the weight ratio of 4,5-dichloro-1,2-dithiol-3-one and N-dodecylguanidine hydrochloride or N-dodecylguanidine acetate is 4:1–1:9.

3. A method of killing or inhibiting the growth of microbes in a water-containing system, which comprises adding a microbicidal/microbistatic controlling amount of (1) 4,5-dichloro-1,2-dithiol-3-one and (2) N-dodecylguanidine hydrochloride or N-dodecylguanidine acetate to said water-containing system.

4. The method as claimed in claim 3, wherein the weight ratio of 4,5-dichloro-1,2-dithiol-3-one and N-dodecylguanidine hydrochloride or N-dodecylguanidine acetate is 95:5–5:95.

5. The method as claimed in claim 4, wherein the weight ratio of 4,5-dichloro-1,2-dithiol-3-one and N-dodecylguanidine hydrochloride or N-dodecylguanidine acetate is 4:1–1:9.

6. The method as claimed in claim 3, wherein the system to be treated is a process water system in papermaking or an industrial cooling water system.

* * * * *